United States Patent [19]

Schreuder

[11] Patent Number: 4,783,332
[45] Date of Patent: Nov. 8, 1988

[54] NOVEL SKIN TANNING COMPOSITION

[75] Inventor: J. C. P. Schreuder, Van Reenenlaan, Netherlands

[73] Assignee: Chemisch Adviesbureau Drs. J.C.P. Schreuder B.V., Baarn, Netherlands

[21] Appl. No.: 64,331

[22] Filed: Jun. 19, 1987

[30] Foreign Application Priority Data

Jul. 7, 1986 [NL] Netherlands ............................ 8601767

[51] Int. Cl.$^4$ .................... A61K 7/021; A61K 7/42; A61K 9/10
[52] U.S. Cl. ........................................ 424/59; 424/60; 424/63; 514/938; 514/939
[58] Field of Search .................................. 424/59, 60

[56] References Cited

U.S. PATENT DOCUMENTS

| | | | |
|---|---|---|---|
| 3,037,015 | 5/1962 | Rudy et al. | 424/59 X |
| 3,230,228 | 1/1966 | Erlemann et al. | 424/59 X |
| 4,349,536 | 9/1982 | Hausler | 424/59 |
| 4,690,774 | 9/1987 | Vishnupad et al. | 514/941 |

FOREIGN PATENT DOCUMENTS

| | | | |
|---|---|---|---|
| 2122291 | 11/1971 | Fed. Rep. of Germany | 424/60 |
| 2326914 | 5/1977 | France | 424/59 |

OTHER PUBLICATIONS

Sagarin Cosmetics Science & Technology, 1957, pp. 192-196, 1113-1117.

Primary Examiner—Dale R. Ore
Attorney, Agent, or Firm—Bierman and Muserlian

[57] ABSTRACT

A skin tanning composition comprising (a) 5 to 50% by weight of an oil fraction of straight or branched paraffinic oils of 10 to 30 carbon atoms with a boiling range of 100° to 500° C. at atmospheric pressure and a viscosity of at most 35 centistokes at 25° C. optionally containing up to 6% by weight of esters of optionally unsaturated higher natural fatty acids and optionally unsaturated natural aliphatic alcohols of up to 20 carbon atoms, (b) 1 to 10% by weight of an emulsifying system comprising (1) 1 to 10% by weight of mono and/or diglycerides of higher optionally unsaturated natural fatty acids and (2) ethoxylated glycerides esterified with fatty acids of the formula

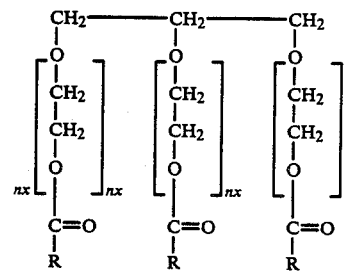

wherein n is an integer from 5 to 20 and the R's are individually an optionally unsaturated fatty acid residue derived from animal or vegetable oils with a ratio of 10 to 100 parts by weight of (1) per part by weight of (2), (c) 1.0 to 5% by weight of a mixture of 2:1 to 1:3 of tyrosine or tyrosine precursor to panthenol, (d) sufficient alkali to maintain the pH of the aqueous phase at 4 to 7, (e) 0.2 to 4% by weight of a montmorillonite stablizer with free oxygen sites occupied by quaternary groups, (f) 0.5 to 1.0% by weight of a preservative for the formed continuous oily phase and the dispersed aqueous phase and (g) water to make up 100% by weight, the weights being based on the weight of the entire composition to effect relatively fast skin tanning upon exposure to natural sun light or from artificial sun tanning equipment such as sunbeds and solaria while avoiding exposure to compounds which can disturb the biological equilibrium of the skin.

10 Claims, No Drawings

NOVEL SKIN TANNING COMPOSITION

STATE OF THE ART

Many compositions have been proposed for skin tanning over the course of the years. Some of these proposed compositions contain as active main ingredient panthenol which is applied in an acid, non aqueous phase, and are indeed effecting the desired skin tanning after exposure to natural or artificial sunlight. However, in the opinion of the modern consumer, the action is too slow. For this reason, compounds which have to protect the skin temporarily against excessive interaction of harmful frequencies in the light spectrum, leading to burning before the actual skin tanning process due to the natural production of melanoprotein (pigment) has taken place in a sufficient degree, have to be incorporated into these skin tanning agents. These so called light filtering agents are still regarded undesirable due to a possible disturbence of the biological equilibrium of the skin and the toxicity of these compounds for humans in large concentrations due to accumulation.

OBJECTS OF THE INVENTION

It is an object of the invention to provide novel tanning compositions containing harmless, fast acting skin tanning agents, wherein the light filtering agents do not need to be used.

It is another object of the invention to provide an improved method of fast tanning of skin.

These and other objects and advantages of the invention will become obvious from the following detailed description.

THE INVENTION

The novel sun tanning compositions of the invention are comprised of (a) 5 to 50% by weight of an oil fraction of straight or branched paraffinic oils of 10 to 30 carbon atoms with a boiling range of 100° to 500° C. at atmospheric pressure and a viscosity of at most 35 centistokes at 25° C. optionally containing up to 6% by weight of esters of optionally unsaturated higher natural fatty acids and optionally unsaturated natural aliphatic alcohols of up to 20 carbon atoms, (b) 1 to 10% by weight of an emulsifying system comprising (1) 1 to 10% by weight of mono and/or diglycerides of higher optionally unsaturated natural fatty acids and (2) ethoxylated glycerides esterified with fatty acids of the formula

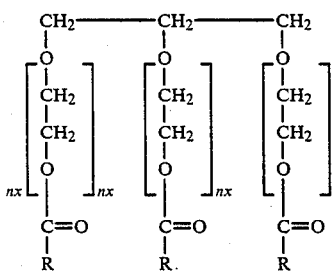

wherein n is an integer from 5 to 20 and the R's are individually an optionally unsaturated fatty acid residue derived from animal or vegetable oils with a ratio of 10 to 100 parts by weight of (1) per part by weight of (2), (c) 1.0 to 5% by weight of a mixture of 2:1 to 1:3 of tyrosine or tyrosine precursor to panthenol, (d) sufficient alkali to maintain the pH of the aqueous phase at 4 to 7, (e) 0.2 to 4% by weight of a montmorillonite stabilizer with free oxygen sites occupied by quaternary groups, (f) 0.05 to 1.0% by weight of a preservative for the formed continuous oily phase and the dispersed aqueous phase and (g) water to make up 100% by weight, the weights being based on the weight of the entire composition.

Preferably, the oil fraction consists of straight or branched parrafinic oils containing 10 to 30 carbon atoms in the chain and preferably 12 to 25 carbon atoms in an amount of 5 to 50% by weight and preferably from 10 to 40% by weight, calculated on the weight of the total system. These paraffinic oils have a boiling range of from 100° to 500° C. at atmospheric pressure and show a viscosity of at most 35 centistokes at 25° C.

The paraffinic oils may be optionally mixed with esters of optionally unsaturated higher natural fatty acids and of higher natural aliphatic alcohols of up to 20 carbon atoms in the chain such as oleyl oleate or oleyl decalate (e.g. Cetiol V ®). The terms "higher natural fatty acids" and "higher natural alcohols" mean fatty acids and alcohols which maybe derived from products occurring in nature such as animal or vegetable oils and fats such as linseed oil, sunflower oil, rape oil, whale oil, castor oil, peanut oil, palm oil, olive oil, coconut oil, soybean oil, tung oil. It appears that for the most effective compositions, these esters are added to the paraffinic oil fractions in an amount up to 6% by weight and preferably 2 to 5% by weight, based on the weight of the total composition.

The emulsifying system mainly consists of (a) mono and/or diglycerides of higher unsaturated and/or saturated natural fatty acids such as linoleic acid, oleic acid, linolenic acid, eleostearic acid, palmitic acid, lauric acid, or mixtures thereof (e.g. Tegomuls ®) in an amount of 1 to 10% by weight and preferably 2 to 8% by weight, calculated on the weight of the complete composition, and (b) ethoxylated glycerides derived from fatty acids of the formula

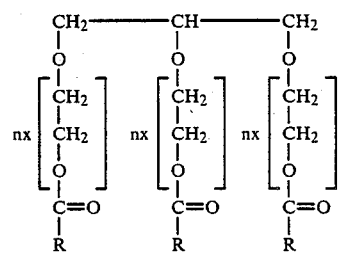

wherein n is a number from 5 to 20 and preferably from 7 to 15 and R is a saturated or unsaturated and preferably unsaturated fatty acid residue derived from vegetable or animal oils, while R may be same or different fatty acid residues in one molecule, but preferably the same (e.g. Tagat TO ®).

It will be appreciated that the emulsifying system only will have to be used in relatively small amounts of the decidedly indispensable, but with reference to skin affections undesired emulsifier, whereas on the other hand the present emulsifying system may be regarded as especially affable to the skin, which feature is connected with a relatively low hydrophilic-lipophylic balance value. The ratio between the amount of the mono and diglycerides and the ethoxylated triglycerides may vary, whereas the advantageous characteristics are maintained, from 10 to 100 parts of mono and diglycerides per part of ethoxylated triglycerides and preferably 25 parts of mono and/or diglycerides per part of ethoxylated triglycerides. The total amount of the emulsifying system, calculated on the weight of the total composition, may vary from 1 to 10% by weight and preferably 2 to 8% by weight, for the most optimal results.

The stabilizer consists of montmorillonites whose free oxygen sites are occupied by quaternary groups (quaternary modified montmorillonites). Examples of such stabilizers which are preferably employed are Bentone ® or Propoloid ® preparations which are added in an amount of from 0.2 to 4% by weight and preferably 0.5 to 2% by weight, calculated on the weight of the total composition. By addition of the said stabilizers, deposit of one or more of the ingredients of the compositions is avoided in the relatively low viscous compositions which are preferred for practical reasons.

Panthenol (provitamin B-5) may be used in one of its pure optical isomeric forms or as a racemic mixture, but preferably as D-panthenol, and tyrosine in one of its pure optical isomer forms or as racemic mixture, but preferably as L-tyrosine, or a compound from which the tyrosine easily may be formed in situ such as e.g. esters of tyrosine or phenylalanine which are known to be readily soluble in the aqueous phase. It will be appreciated that it is generally known that phenylalanine can be easily converted into tyrosine under natural conditions.

With regard to the known poor solubility of tyrosine as such in an aqueous phase, the good properties of the present compositions could certainly not be expected or predicted by people skilled in the art. Tyrosine is preferably added in the form of lower alkyl esters such as methyl, ethyl, (iso)propyl or (iso)butyl ester or in the form of the stearyl ester or the benzyl ester wherein the amino group optionally may be temporarily protected in a known way and is preferably protected by HCl addition.

Additionally, it was found that the aqueous phase wherein the panthenol and the tyrosine ester ultimately have to be present may have a pH in the range of 4 to 7 and more preferably in the range of 4 to 6 which may be obtained by addition of suitable alkaline agent such as sodium citrate and/or sodium hydroxide, especially in the case of protection of the amino group by HCl addition. The amounts of e.g. sodium citrate and/or sodium hydroxide will vary, depending on the specific protecting groups in the starting tyrosine derivative from 0.1 to 3% by weight, calculated on the weight of the complete composition.

The molar ratio of tyrosine and panthenol should be in the range from 2:1 to 1:3 to reach the indicated attractive properties of the compositions of the invention while the amounts of panthenol and tyrosine or tyrosine providing means should be 1 to 5% by weight (and preferably 2 to 4% by weight) and 0.5 to 5% by weight (preferably 1 to 4% by weight) respectively, calculated on the weight of the complete composition.

The preservative is preferably selected from different types of preservatives which can be used for the ultimately formed continuous oily phase and the dispersed aqueous phase. For example, esters of p-hydroxy benzoic acid are used for the oily phase and preferably the methyl and/or the (iso)propyl ester and/or (iso)butyl ester is used in an amount of 0.05 to 1% by weight, calculated on the weight of the complete composition, and preferably in an amount of 0.2 to 0.4% by weight. Preferred are mixtures of methyl, propyl and butyl-p-hydroxy-benzoate (e.g. Phenonip ®). It will be appreciated that the said preservatives may be completely or partially replaced by other preservatives (e.g. Germall 115 ® or Hydroconserv ®) in an amount of 0.05 to 1% by weight and preferably 0.2 to 0.4% by weight in the dispersed aqueous phase.

In addition to the beforementioned primary indispensable ingredients, one or more secondary ingredients also can be added to the final composition if desired, such as: (a) vitamin E as such or preferably in the relatively stable acetate form in an amount of 0.05 to 5% by weight calculated on the weight of the complete composition and preferably in an amount of from 0.2 to 2% by weight. (b) glycerol in an amount of 0.5 to 5.0% by weight, calculated on the weight of the complete composition and preferably in an amount of from 1 to 3% by weight, to form a moisture regulating system, together with the panthenol and optionally co-added sodium lactate and/or possibly alkali to maintain the desired pH of from 4 to 7 such as sodium citrate. The total amount of alkali such as sodium citrate, sodium hydroxide and optional sodium lactate will vary from 0.1 to 5% by weight. (c) a gelforming agent such as carraghenate, preferably consisting of a polysaccharide bearing sulfonic acid residues, and preferably those of natural origin such as those derived from seaweed. The sulfonic acid residues have optionally been converted into salts or esters of glycol, propylene glycol and glycerol (the so called modified carraghenates).

The beforementioned carraghenates cause a gel structure in the final complete composition in the amounts of from 0.1 to 5% by weight, calculated on the weight of the complete composition, and preferably 0.5 to 2% by weight. Such a complete composition shows a viscosity of 200 to 5000 centipoises at 25° C. which is desired for an adequate application of the composition. It will be appreciated by a person skilled in this specific art, that the carraghenate may be completely or partially replaced by alternative gel forming means, such as carboxy methyl cellulose, esterified by polyacrylic acid (e.g. Carbopol ®) or hydroxy ethyl cellulose, in amounts which lead to viscosity values situated in the beforementioned range.

Also useful are (d) perfume, in an amount of from 0.1 to 0.5% by weight, calculated on the weight of the complete composition. (e) anti oxidants in an amount of from 0.01 to 3% by weight, calculated on the weight of the complete composition. (f) an alkanol, and more preferably ethanol (96%) in an amount of from 0.1 to 1.0% by weight and preferably 0.3 to 0.6% by weight, calculated on the weight of the complete composition. The alkanol may be added to reach a fast gelation of the quaternary modified montmorillonites.

The compositions of the invention are characterized by a relatively low viscosity and high stability which guarantees an easy application without a "greasy" feeling or stickiness and stains in clothes due to a fast penetration into the skin tissue, and they give the skin the desired tanning by means of natural pigment formation in the skin after a relatively short period of exposure to light.

The compositions of the invention may be prepared by a process which should be regarded as another aspect of the invention which is characterized by a specific sequence of addition and the dosing rate of the respective beforementioned ingredients and by the temperature and stirring speeds at which this addition c.q. dosing takes place.

The first step of the process comprises the preparation of the complete continuous oily phase composed of the oil fractions, the esters of the unsaturated fatty acids and alcohols, emulsifying system, stabilizers, preservatives and alkanol, e.g. ethanol while the dispersed aqueous phase is composed of water, glycerol, panthenol, tyrosine or tyrosine providing compound, desired alkali and carraghenate. Vitamin E and the possible perfume may be added to the prepared emulsion.

The compositions of the invention are preferably preferred by mixing both phases together at a temperature of at most 30° C., followed by additional stirring after the possible addition of Vitamin E and perfume until an average particle size of the dispersed aqueous phase is at most $5\mu$, and preferably smaller than $3\mu$.

It will be appreciated by a person skilled in the art that the application of the said compositions, i.e. the treatment of the skin with the before described compositions, forms another aspect of the invention. Such an application comprises a method usual for such compositions characterized by application and spreading evenly onto the skin area involved of an amount of 20 to 100 ml/m² skin area, if necessary after thorough cleaning of the skin with water and soap or an alcoholic solution, preceeding the exposure of the skin to natural or artificial sunlight. This treatment should be preferably be repeated 2 to 3 times a day.

In the following examples there are described several preferred embodiments to illustrate the invention. However, it should be understood that the invention is not intended to be limited to the specific embodiments.

EXAMPLE 1

The following ingredients are combined with stirring and the mixture was cooled to at most 30° C.

| | | |
|---|---|---|
| Paraffinic oil I (Shell Ondina 15 ®, boiling range 295 to 390° C.) | 130 g | |
| Paraffinic oil II (Shell Ondina 68 ®, boiling range 290 to 500° C.) | 30 g | |
| Mono and/or diglycerides (Tegomuls ®) | 25 g | oily phase |
| Oleyl decalate (Cetiol V ®) | 30 g | |
| Ethoxylated triglycerides (Tagat TO ®) | 1 g | |
| Preservatives I (Phenonip ®) | 2 g | |
| followed by addition of quaternary modified montmorillonites (Bentone 38 ®) | 6 g | |
| and gelation by addition of 96% ethanol | 3 g | |

The aqueous phase was prepared by dissolving the following ingredients in 687 g of water

| | | |
|---|---|---|
| Glycerol | 20 g | |
| Phenyl alanine | 20 g | |
| Sodium citrate | 10 g | aqueous phase |
| D-panthenol | 16 g | |
| Preservative II (Hydroconserv ®) | 3 g | |
| Carraghenate | 5 g | |

The resulting aqueous phase was then mixed with the oily phase and homogenized after addition of 10 g of vitamin E-acetate (D-isomer) and 2 g of perfume. The water-in-oil emulsion was further homogenized until an average particle size $<3\mu$ was reached.

EXAMPLE 2

Using the procedure of Example 1, a composition was prepared from the following ingredients:

| | | |
|---|---|---|
| Paraffinic oil I | 250 g | |
| Paraffinic oil II | 50 g | |
| Mono and/or diglycerides | 40 g | |
| Ethoxylated triglycerides | 2 g | oily phase |
| Preservative I | 2 g | |
| Quaternary modified montmorillonites (Bentone 27 ®) | 6 g | |
| Ethanol | 3 g | |
| and | | |
| Water | 580 g | |
| Glycerol | 15 g | |
| L-tyrosine ethylate HCl | 10 g | |
| Sodium Hydroxide | 1 g | aqueous phase |
| D-panthenol | 10 g | |
| Sodium lactate | 10 g | |
| Preservative I | 3 g | |
| Carraghenate | 8 g | |
| and | | |
| Vitamin E-acetate (D-isomer) | 8 g | |
| Perfume | 2 g | |

EXAMPLE 3

Using the procedure of Example 1, a composition was prepared from the following ingredients:

| | | |
|---|---|---|
| Paraffinic oil I | 150 g | |
| Paraffinic oil II | 40 g | |
| Mono and/or diglycerides | 30 g | |
| Ethoxylated triglycerides | 1 g | |
| Oleyl oleate | 20 g | oily phase |
| Preservative I | 2 g | |
| Quaternary modified montmorillonites (Bentone 38 ®) | 6 g | |
| Ethanol | 2 g | |
| and | | |
| Water | 659 g | |
| Glycerol | 15 g | |
| L-tyrosine isobutylate | 30 g | aqueous phase |
| Sodium citrate | 10 g | |
| D-panthenol | 20 g | |
| Preservative III (Euxyl 100 ®) | 3 g | |
| and | | |
| Vitamin E-acetate (D-isomer) | 10 g | |
| Perfume | 2 g | |

EXAMPLE 4

Using the procedure of Example 1, a composition was prepared from the following ingredients:

| | | |
|---|---|---|
| Paraffinic oil I | 140 g | |
| Paraffinic oil II | 25 g | |
| Mono and/or diglycerides | 15 g | |
| Oleyl decalate | 26 g | |
| Ethoxylated triglycerides | 0.5 g | oily phase |
| Preservative I | 3 g | |
| Quaternary modified montmorillonites (Bentone 27 ®) | 7 g | |
| Ethanol | 3 g | |
| and | | |
| Water | 692.5 g | |
| Glycerol | 20 g | |
| L-tyrosine ethylate HCl | 15 g | |
| Sodium hydroxide | 10 g | aqueous phase |
| D-panthenol | 15 g | |
| Sodium lactate | 4 g | |
| Sodium citrate | 3 g | |
| Preservative I | 3 g | |
| Carraghenate | 8 g | |
| and | | |

-continued

| | |
|---|---|
| Vitamin E-acetate (D-isomer) | 7 g |
| Perfume | 3 g |

EXAMPLE 5

Using the procedure of Example 1, a composition was prepared from the following ingredients:

| | | |
|---|---|---|
| Paraffinic oil I | 200 g | |
| Paraffinic oil II | 50 g | |
| Mono and/or diglycerides | 40 g | |
| Ethoxylated triglycerides | 2 g | oily phase |
| Preservative I | 2 g | |
| Quaternary modified montmorillonites (Benton 2 ®) | 6 g | |
| Isopropanol | 2 g | |
| and | | |
| Water | 613 g | |
| Glycerol | 15 g | |
| D,L-tyrosine isobutylate | 25 g | aqueous phase |
| D,L-Panthenol | 20 g | |
| Sodium citrate | 10 g | |
| Preservative III | 3 g | |
| Vitamin E-acetate (D,L) | 10 g | |
| Perfume | 2 g | |

The said compositions caused a fast, intensive natural skin tanning within some hours of exposure after the application in the usual way.

Various modifications of the compositions and methods of the invention may be made without departing from the spirit or scope thereof and it is to be understood that the invention is intended to be limited only as defined in the appended claims.

What is claimed is:

1. A skin tanning composition comprising (a) 5 to 50% by weight of an oil fraction of straight or branched paraffinic oils of 10 to 30 carbon atoms with a boiling range of 100° to 500° C. at atmospheric pressure and a viscosity of at most 35 centistokes at 25° C. containing 0 to 6% by weight of esters of saturated or unsaturated higher natural fatty acids and saturated or unsaturated natural aliphatic alcohols of up to 20 carbon atoms, (b) 1 to 10% by weight of an emulsifying system comprising (1) 1 to 10% by weight of mono and/or diglycerides of higher saturated or unsaturated natural fatty acids and (2) ethoxylated glycerides esterified with fatty acids of the formula

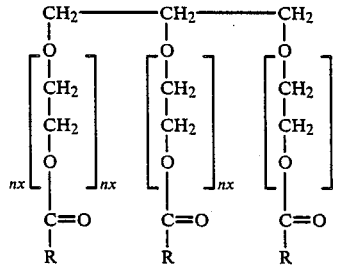

wherein n is an integer from 5 to 20 and the R's are individually a saturated or unsaturated fatty acid residue derived from animal or vegetable oils with a ratio of 10 to 100 parts by weight of (1) per part by weight of (2), (c) 1.0 to 5% by weight of a mixture of 2:1 to 1:3 of tyrosine or tyrosine precursor to panthenol, (d) sufficient alkali to maintain the pH of the aqueous phase at 4 to 7, (e), 0.2 to 4% by weight of a montmorillonite stabilizer with free oxygen sites occupied by quaternary groups, (f) 0.05 to 1.0% by weight of a preservative for the formed continuous oily phase and the dispersed aqueous phase and (g) water to make up 100% by weight, the weights being based on the weight of the entire composition.

2. A composition of claim 1 wherein (a) the paraffinic oils have 15 to 25 carbon atoms and the oil fraction is 10 to 40% by weight of the composition, (b) $\eta$ is an integer from 7 to 15, (c) the panthenol is D-panthenol and the tyrosine is L-tyrosine and the amount of each of these components is 0.5 to 5% by weight, (d) the pH is 4 to 6 and the alkaline agent is sodium citrate and/or sodium hydroxide.

3. A composition of claim 1 wherein it further contains at least one ingredient selected from the group consisting of vitamin E in an amount of 0.05 to 5% by weight, glycerol in an amount of 0.5 to 5.0% by weight, alkanol in an amount of 0.1 to 1.0% by weight, sodium lactate in an amount of 0.1 to 5% by weight, gel forming agent in an amount of 0.1 to 5% by weight, perfume in an amount of 0.1 to 0.5% by weight and antioxidants in an amount of 0.01 to 3% by weight, calculated on the weight of the complete composition.

4. A composition of claim 1 wherein it contains an oil fraction in an amount of 10 to 40% by weight.

5. A composition of claim 1 wherein the oil fraction is mixed with oleyl oleate or oleyl decalate in an amount of 2 to 5% by weight, calculated on the weight of the complete composition.

6. A composition of claim 1 wherein the emulsifying system is composed of ethoxylated triglycerides derived from linoleic acid, oleic acid, linolenic acid or mixtures thereof mixed with mono and/or diglycerides derived from linoleic acid, linolenic acid, oleic acid, palmitic acid, lauric acid, myristic acid, stearic acid, eleostearic acid and mixtures thereof.

7. A composition of claim 1 wherein the ratio between mono and/or diglycerides and ethoxylated triglycerides is 25 parts mono and/or diglycerides per part of ethoxylated triglycerides.

8. A composition of claim 1 wherein the preservative in the oily phase is at least one ester of p-hydroxybenzoic acid in an amount of 0.2 to 4% by weight.

9. A process for the preparation of a composition of claim 1 comprising preparing an oily phase by addition of the emulsifying system, preservative and stabilizer to the oily components with stirring and heating until gelation after addition of alcohol followed by cooling to at most 30° C. and addition of the aqueous phase composed of water, preservative, glycerol, panthenol, tyrosine or tyrosine providing compound sufficient alkali and carraghenate.

10. In a method of tanning skin, the improvement comprising applying 20 to 100 ml/m$^2$ skin area of a composition of claim 1 to the skin area involved and then subjecting the skin to the exposure of natural or artificial sunlight.

* * * * *